United States Patent [19]

Stubbs et al.

[11] Patent Number: 5,723,750
[45] Date of Patent: Mar. 3, 1998

[54] TRANSGENIC PLANTS EXPRESSING DISASSEMBLY DEFICIENT VIRAL COAT PROTEINS

[75] Inventors: Gerald Stubbs, Nashville, Tenn.; James N. Culver, Silver Spring, Md.

[73] Assignees: Vanderbilt University, Nashville, Tenn.; Univ. of Maryland Biotechnology Institute, College Park, Md.

[21] Appl. No.: 372,175

[22] Filed: Jan. 12, 1995

[51] Int. Cl.$^6$ .............................. A01H 5/00; C12N 15/33; C12N 15/84
[52] U.S. Cl. .................. 800/205; 435/69.1; 435/172.1; 435/172.3; 435/320.1; 536/23.1; 536/23.72
[58] Field of Search .................. 800/205; 435/172.1, 435/172.3, 69.1, 240.4, 320.1; 536/23.1, 23.72

[56] References Cited

U.S. PATENT DOCUMENTS

| | | | |
|---|---|---|---|
| 4,970,168 | 11/1990 | Tumer | 435/317.1 |
| 5,185,253 | 2/1993 | Tumer | 435/172.3 |

OTHER PUBLICATIONS

Culver et al., "Site-Directed Mutagenesis Confirms the Involvement . . . ," *Virology* 206:724–730, 1995 (no month or day given).

Stubbs et al., Abstract, "Tobacco mosaic virus: structure, assembly, and disassembly," FASEB Conference on Viral Assembly, Saxtons River, Vermont, held Jul. 26–31, 1992.

I. Potrykus, "Gene Transfer to Plants: Assessment . . . ," *Ann. Rev. Plant Physiol. Plant Mol. Biol.* 42:205–225, 1991 (no month or day given).

Schardl et al., "Design & construction of a versatile system . . . ," *Gene* 61:1–11, 1987 (no month or day given).

Wilson, T.M.A. (1993) Proc. Natl Acad Sci USA 90:3134–3141.

Nejidat et al (1990) Physiologia Plantarum 80:662–668.

Register et al (1988) Virology 166:524–532.

*Primary Examiner*—Elizabeth McElwain
*Attorney, Agent, or Firm*—Needle & Rosenberg, P.C.

[57] ABSTRACT

The present invention provides a method for protecting plants against infection by pathogenic plant viruses comprising administering to the plant a nucleic acid, encoding a pathogenic plant virus protein, containing substitutions in the genetic sequence which result in the replacement of amino acids having carboxylate side chains with uncharged amino acids and which have the phenotypic effect of displacing wild type coat proteins in a wild type virus and inhibiting the ability of the wild type virus to disassemble under conditions whereby the nucleic acid is expressed as a mutant coat protein within the plant. Also provided is a nucleic acid, encoding a pathogenic plant virus protein, containing substitutions in the genetic sequence which result in the replacement of amino acids having carboxylate side chains with uncharged amino acids and which have the phenotypic effect of displacing wild type coat proteins in a wild type virus and inhibiting the ability of the wild type virus to disassemble.

5 Claims, No Drawings

TRANSGENIC PLANTS EXPRESSING DISASSEMBLY DEFICIENT VIRAL COAT PROTEINS

ACKNOWLEDGEMENTS

This invention was made with government support under grant number MCB-920790 awarded by the National Science Foundation. The government has certain rights in the invention.

BACKGROUND OF THE INVENTION

1. Field of the invention

The present invention generally provides a method for protecting plants against infection by pathogenic plant viruses. Specifically, the method utilizes mutant viral coat proteins, expressed in transgenic plants, which displace wild type coat proteins of infecting viruses and inhibit their disassembly.

2. Background Art

Virus diseases of cultivated plants cause substantial reductions in food, forage and fiber throughout the world. Control of these diseases has been based primarily on cultural practices that include removal of viral infected debris, eradication of weed hosts (herbicide applications), prevention of vector transmission (pesticide applications), indexing for virus-free starting material (seed or vegetative propagules) and breeding for disease resistance (1). Large scale methods for curing plants once they have become virus infected do not exist. Thus, the control of viral diseases is dependent upon methods to prevent or delay the establishment of infection.

Of the above disease control measures, breeding for resistance is generally one of the most economical and practical methods, as it requires no additional labor or expense to the grower. Moreover, controlling viral diseases with resistance does not require applications of herbicides or pesticides to eliminate weed hosts and insect vectors. Thus, host resistance is one of the most environmentally safe and durable methods for controlling plant diseases. Unfortunately, in many plant-virus systems, resistance is not available and cannot be obtained using traditional plant breeding strategies. However, recent advances in molecular biology and gene manipulation have proven helpful in integrating new disease resistance factors into plant-virus systems where none existed before.

The development of transgenic plants has proven to be a valuable molecular strategy for protecting plants from viral diseases. In particular, transgenic plants expressing wild type coat proteins of at least eight different virus groups have been shown to provide varying levels of resistance to infection by the corresponding virus (2, 3). The mechanisms behind conferred resistance have not been established. However, on the basis of experimental data, it is likely that different and/or multiple mechanisms exist in each system. Proposed mechanisms include transgene coat protein interference with viral disassembly, transgene RNA interference with viral replication and transgene activated plant RNA degradation systems (4, 5).

In several systems, including tobacco mosaic virus (TMV), cucumber mosaic virus and potato virus X, resistance conferred by the transgene expression of wild type coat protein is more difficult to overcome than resistance conferred by the expression of RNA alone. This suggests that coat protein plays a role in mediating this resistance. The best studied system is TMV coat protein-mediated resistance. In general, this increased resistance is observed as a reduction in the numbers of infection sites on inoculated leaves, indicating that an initial step in the virus life cycle has been disrupted (6). In addition, only transgenic plants that accumulate coat protein show levels of resistance, while transgenic plants that do not accumulate coat protein remain susceptible (7). Another unique feature of this system is that resistance is overcome by inoculating transgenic plants with infectious uncoated viral RNA (7). This evidence indicates that transgene coat protein may act to prevent initial disassembly of infecting viral particles thus disrupting the disease cycle (4). Thus, if interference by coat proteins with viral disassembly is an important mechanism by which resistance to infection is conferred, it appears to be necessary that the coat protein readily dissociate from aggregates with itself in order to associate with infecting virus particles and interfere with the disassembly of the infecting virion.

Unfortunately, in many of these systems, the resistance conferred by transgenic coat expression is only effective against low levels of viral inoculum and leads to only a delay in disease development. For example, TMV resistance is significantly reduced when virion inoculum levels are increased from 0.4 ug/ml to 2.0 ug/ml (2).

On the basis of the three dimensional structure of the rod shaped TMV, mutant coat proteins were originally made for the purpose of studying the process of viral disassembly (8). The rationale behind these experiments at the time was to study disassembly and these studies were not designed to specifically examine the ability of the routants to inhibit infection. Furthermore, these studies indicated a degree of inhibition of disassembly of viruses containing the mutant coat proteins that would not have been considered to be sufficient to impart protection to plants.

Contrary to the findings in the art, this invention demonstrates that excess mutant TMV coat protein can inhibit wild type virus disassembly to a much greater degree than that observed with excess wild type coat protein. This result was determined even though the mutant proteins demonstrate the potential for forming stable aggregates with themselves which would make them less likely than wild type coat proteins to be available to inhibit disassembly of infecting wild type virus.

Thus, this invention improves the prior art by providing a method for creating transgenic plants with enhanced resistance which express mutant viral coat proteins which displace wild type viral coat proteins and inhibit virus disassembly to a greater degree than that demonstrated with transgene expressed wild type viral coat proteins.

An additional aspect of the present invention is that transgenic plants expressing mutant coat proteins are less hazardous to the environment because virus particles containing mutant coat proteins are very ineffective in infectivity. Furthermore, recombination between a challenge virus and a transgene coat protein that is dysfunctional in disassembly would result in a virus that is less fit and therefore less likely to survive in nature. Thus, mutant coat protein genes would pose no threat in the wild.

SUMMARY OF THE INVENTION

The present invention provides a method for protecting plants against infection by pathogenic plant viruses comprising administering to the plant a nucleic acid, encoding a pathogenic plant virus protein, containing substitutions in the genetic sequence which result in the replacement of amino acids having carboxylate side chains with uncharged amino acids and which have the phenotypic effect of displacing wild type coat proteins in a wild type virus and inhibiting the ability of the wild type virus to disassemble under conditions whereby the nucleic acid is expressed as a mutant coat protein within the plant.

Also provided is a nucleic acid, encoding a pathogenic plant virus protein, containing substitutions in the genetic sequence which result in the replacement of amino acids having carboxylate side chains with uncharged amino acids and which have the phenotypic effect of displacing wild type coat proteins in a wild type virus and inhibiting the ability of the wild type virus to disassemble.

DETAILED DESCRIPTION OF THE INVENTION

The present invention may be more readily understood by reference to the following detailed description of specific embodiments and the Examples included therein.

As used in the claims, "a" can mean one or more, depending on the context in which it is used.

The present invention provides a method for protecting plants against infection by pathogenic plant viruses comprising administering to the plant a nucleic acid, encoding a pathogenic plant virus protein, containing substitutions in the genetic sequence which result in the replacement of amino acids having carboxylate side chains with uncharged amino acids and which have the phenotypic effect of displacing wild type coat proteins in a wild type virus and inhibiting the ability of the wild type virus to disassemble under conditions whereby the nucleic acid is expressed as a mutant coat protein within the plant.

As used herein, "pathogenic plant virus" means a virus which infects plants and produces a condition considered to be abnormal and detrimental to the plant. Such viruses would typically consist of a genomic nucleic acid enclosed by coat protein subunits assembled around the nucleic acid in a specific geometric conformation, which are partially or completely removed during the disassembly phase of infection to expose the nucleic acid. Also as used herein, "substitutions in the genetic sequence" means site specific point mutations introduced by methods widely known in the art which result in the substitution of specific nucleotides for other specific nucleotides in the genetic sequence of the coat protein gene such that the nucleic acid encodes a mutant coat protein that can inhibit, to a greater degree than a wild type coat protein, the ability of a wild type virus to disassemble.

The present invention further provides a nucleic acid, encoding a pathogenic plant virus protein, containing substitutions in the genetic sequence which result in the replacement of amino acids having carboxylate side chains with uncharged amino acids and which have the phenotypic effect of displacing wild type coat proteins in a wild type virus and inhibiting the ability of the wild type virus to disassemble. The nucleic acid can be incorporated into any suitable gene transfer vector, such as, for example, the binary Agrobacterium vector pKyLx71, the pMON series of vectors (Monsanto) and the pBIN series of vectors (Clonetech). Other suitable transfer vectors can be constructed according to the standard teachings in the art (9, 30). The nucleic acid can be introduced into the plant cells by any method known to one of skill in the art to introduce nucleic acid into cells, including, but not limited to Agrobacterium mediated gene transfer, particle acceleration (10) and electroporation. Proteins encoded by these nucleic acids are also provided. These proteins can be in a purified form.

Structural Interpretation

Knowledge of the three-dimensional structure of the virus is a key aspect of the present invention because it permits identification of the location of closely associated glutamate and/or aspartate residues, which play a crucial role in viral disassembly. The three-dimensional atomic structure of the virus or of an aggregate of its coat protein is determined by the methods of fiber diffraction in the case of a rigid rod-shaped virus, or by the methods of crystallography in the case of a spherical virus or an aggregate of the coat protein of any type of virus.

Fiber diffraction: An oriented gel of the virus is made by applying shearing forces to a solution of the virus in a glass capillary (11). All subsequent steps have been described by Namba and Stubbs (12), or by Namba et at. (13). In brief, the gel is exposed to a beam of x-rays and the scattering pattern of x-rays generated is measured by any standard method, for example, on photographic film. Scattering patterns are also measured from gels in which the virus has been reacted with salts of heavy metals such as mercury or lead. The exact number of patterns to be measured varies from one virus to another, but in the case of TMV, patterns from the unreacted virus and six heavy metal derivatives were required. The spatial distributions of the intensities in the scattering patterns are combined to calculate a distribution of the electrons in the virus and this electron distribution is interpreted to obtain a model of the positions and identities of the atoms in the virus, including glutamate and/or aspartate residues in the coat protein.

Crystallography: Crystals of the virus or the coat protein are obtained by well-known procedures, such as those described by McPherson (14). X-ray scattering patterns from the virus and one or two heavy metal derivative crystals are measured and the data used to calculate an electron distribution. Knowledge of electron distribution permits the localization and identification of glutamate and/or aspartate residues. Procedures for calculating electron distributions from virus or protein crystal data are well known and are given, for example, by Abad-Zapatero et al. (15) and by Silva and Rossman (16).

The above methods can be broadly applied to any plant virus preparation. By this means, the location of glutamate and/or aspartate residues that are relevant to the disassembly of viruses can be determined for any virus. This information is then used to design the mutants of the present invention.

Mutant Design

In many viruses, particularly plant viruses, two or more residues of the amino acids aspartate and/or glutmate (having carboxylate side chains) occur close together in the three-dimensional structure of the virus. The mutual repulsion between these closely spaced residues causes the disassembly of the virus, an essential step in viral infection, under appropriate conditions. Carboxylate groups have been found at subunit interfaces in the structures of many plant viruses (17), often forming calcium binding sites. Examples include but are not limited to the spherical viruses tomato bushy stunt virus, southern bean mosaic virus and satellite tobacco necrosis virus, as well as the rod-shaped TMV. Interactions between carboxylate groups provide a sensitive switch, active under physiological conditions, to control the state of aggregation of the virus proteins. Electrostatic interactions, particularly in the form of mutual repulsion by carboxylate groups, have been recognized for many years to be important in the assembly and disassembly of simple helical and spherical plant viruses (18, 19).

Viral coat proteins contain many aspartate and glutmate residues, however, and most are not involved in disassembly. The correct residues can be identified by examining the three-dimensional structure and identifying closely-spaced glutmate and/or aspartate residues from different coat protein molecules. These residues must be replaced by the corresponding amide residues (asparagine for aspartate, glutamine for glutmate), by site-directed mutagenesis.

As an example, the structure of TMV has been extensively studied and is known to contain two unusually close approaches between carboxylate side chains from neighboring subunits (Glu50/Asp77 and Glu95/Glu106) and one close approach between a carboxylate group (Asp116) and a phosphate group from the RNA. It is believed that the early stages of viral disassembly are driven by electrostatic repulsions within the two carboxyl-carboxylate pairs and the phosphate-carboxylate pair.

As representative of the infection process of a plant virus, the early stages of TMV infection can be described as follows (13). After the initial entry of the virion into the cell, the low calcium concentration and high pH (relative to the extracellular environment) remove protons and calcium ions from the carboxyl-carboxylate and carboxylate-phosphate pairs, allowing electrostatic repulsive forces from the negative charges to destabilize the virus. This destabilization is sufficient to expose the first start codon of the RNA. After destabilization, ribosomes can bind RNA in competition with the coat protein, completing the uncoating of the RNA in a process called cotranslational disassembly (20).

Replacement of the members of the carboxyl-carboxylate pairs in the coat protein subunit interface by the corresponding amides results in greater stabilization of protein-protein interactions in the viral coat. As a result, these types of mutations yield viral coat proteins which form viruses defective in their uncoating ability and which can displace wild type coat proteins during the uncoating of wild type viruses, inhibiting disassembly of wild type virions during infection.

The ability of the mutant coat proteins to suppress disassembly of wild type virus demonstrates that disassembly is at least partially a reversible process. Subunits of mutant protein can bind to a partially disassembled virion, forming a complex much more stable than the wild type partially disassembled virion and thus, effectively inhibiting further disassembly. For example, disassembly of the TMV virions begins at the 5' end of the RNA (34) and the exposed disassembling face contains Asp77, but not Glu50. An incoming subunit of the mutant, TMV-E50Q (which contains a Glu50 –>Gln substitution), will bind very strongly to the exposed face, forming an intersubunit hydrogen bond between Gln50 and Asp77, but making no repulsive electrostatic interaction. The complex will, thus, be much more stable than the complex of wild type subunits. An incoming subunit of the mutant, TMV-D77N (which contains an Asp77->Asn substitution), in contrast, will make wild-type interactions with the exposed face, including the normal repulsive interaction between Asp77 (from the wild type protein) and Glu50 (from the mutant protein). TMV-D77N may have a stabilizing effect due to the binding of a wild type or TMV-D77N protein subunit to the already bound TMV-D77N subunit, but this effect will be second order and much smaller than the direct effect seen in TMV-E50Q. The ability of the mutant coat protein TMV-E50Q to reduce the infectivity of wild type TMV is consistent with its ability to suppress wild type TMV disassembly and probably involves the exchange of the mutant and wild type protein subunits under the partially disassembling conditions of incubation.

Gene Construction and Virus Purification

Site-directed mutagenesis is achieved by well-known and widely used standard methods (22). For example, uracil-containing single-stranded template can be obtained by coinfection of the virus with phage M13KO7 in *Escherichia coli* strain CJ236 (23). Second-strand synthesis can be performed using synthetic oligomers 18 nucleotides in length. Each oligomer can contain a single mismatched base from the coat protein gene sequence (24). In vitro transcriptions of full-length clones can be performed as described by Ahlquist and Janda (25) and by Dawson et at. (26). Transcription products can be inoculated directly onto the leaves of the systemic host. Infected tissue can be harvested after ten days and virions extracted by differential centrifugation methods, as described by Gooding and Hebert (27). Coat proteins can be isolated from virus preparations by treating with acetic acid (28).

Several variations of mutations can also be investigated to enhance deficiencies in virion disassembly. One variation can be to create a coat protein with all interactive carboxyl-carboxylate/phosphate pairs removed such that destabilization due to repulsive negative charges does not occur within any region of the virion. Another variation is to replace one negatively charged carboxyl-carboxylate member with a positively charged residue such as lysine. In this manner, the negative charge from one side of the pair will be permanently stabilized by the positive charge of the corresponding lysine residue. This should produce a coat protein with extremely strong protein-protein or protein-RNA binding that would be highly resistant to disassembly.

All mutants can be tested to determine if the designed mutations affect virion disassembly in the following manner:

1. Determine ability to move systemically within the systemic host. Reduced systemic movement has been shown to correspond to reduced virion assembly and/or disassembly.

2. Determine particle formation by electron microscopy. Disassembly deficient routants usually form ion-like particles.

3. Test purified virions for the level of contained RNA and reduced infectivity. Higher levels of empty virions, containing no RNA, and reduced overall infectivity has been correlated with coat proteins deficient in disassembly.

4. Test purified mutant coat proteins for their ability to inhibit wild-type virion disassembly both in vitro and in vivo.

The above experiments can be used to clearly identify those mutations that have a detrimental affect on virion disassembly and are thus suitable for use in generating transgenic plants. Additional methods such as the screening method described below can be used to determine the level of effectiveness of a given mutation in inhibiting disassembly.

Screening

Mutant coat proteins can be screened by disassembling wild-type virus in the presence of mutant protein and measuring the rate at which RNA nucleotides are exposed to the action of ribonuclease. For example, solutions containing wild-type virus and mutant coat protein can be incubated under disassembly conditions (e.g., high pH, high salt) for several hours, ribonuclease can be added under conditions favorable to digestion of exposed RNA and the concentration of released nucleotides can be determined by measuring the absorption of 260 nm wavelength light. The genes of those coat proteins that strongly inhibit wild-type viral disassembly are used to construct transgenic plants.

Transgenic Plants

Coat proteins which inhibit virion disassembly in vivo and in vitro can be tested for their ability to confer resistance in transgenic plants. This will require the integration of each coat protein open reading frame (ORF) into the genome of a host plant via a suitable gene transfer. Altered as well as wild-type coat protein ORFs or nucleotides can be inserted into the appropriate vector, (e.g., the polylinker region of the binary Agrobacterium vector pKyLx71 (9)). Constructs should contain only coat protein ORF sequences. This should help minimize any effects on resistance due to the presence of other viral sequences, such as the 3' end. Coat protein transcription can be controlled, for example, by the cauliflower mosaic virus 35S promoter and polyadenylation derived, for example, from the ribulose-1,5-bisphosphate carboxylase small subunit gene. A second transformation vector pKyLx7:35S$^2$ containing tandem 35S promoters for enhanced transcription can also be used (29). Transformation and cell regeneration can be done on leaf disks using established protocols (30). This and other methods, and the relevant controls can be adapted for a variety of viruses once the pertinent mutants are designed and constructs made as described herein.

Controls. Several control transgenic plant lines can also be created and tested in parallel with wild-type and disassembly deficient coat protein constructs. First, vector only transgenic plants can be produced to identify vector mediated affects on resistance levels and to serve as a baseline for measuring any increase in resistance conferred by other constructs. Second, a mutant coat protein ORF in which the translational start codon is altered to prevent coat protein expression can also be used as a transgene construct (31). This defective ORF will express gene sequences but not produce coat protein. Thus, any effects on resistance from coat protein ORF gene sequences can also be identified. Finally, transgenic plants expressing coat protein mutants can also be created that are predicted to disrupt overall coat protein structure. For example, coat protein mutants F48S and R71L have been shown to be incapable of virion or large aggregate assembly (32). The transgenic plants expressing mutant coat proteins that are incapable of virion/aggregate assembly should not confer resistance.

Measuring Levels of Resistance

Levels of conferred resistance for each transgene construct can be determined. In particular, levels of resistance can be measured in relation to the levels of virus inoculum. Two leaves per plant can be inoculated with 0.5 ug of purified virus for initial resistance comparisons between wild-type, mutant and control transgenic plants. Both mutant and wild-type transgenic lines should show resistance at this level of inoculum. Test plants can be inoculated at the four to five leaf stage of development and observed for the appearance of mosaic symptoms in the upper non-inoculated leaves. Non-transformed plants inoculated with 0.5 ug of TMV should show easily identifiable mosaic symptoms 5 to 7 days post-inoculation. Additionally, sap extracts from upper non-inoculated leaves can be inoculated onto the viral local lesion host and subjected to ELISA specific for the detection of the virus. Thus, the presence of a viral infection in the absence of visual symptoms can also be determined. For resistance experiment, plants can be observed for at least four weeks post-inoculation.

If disassembly deficient coat proteins show higher levels of resistance per amount of expressed coat protein, then additional assays can be done using sequentially (1 ug to 1 mg) higher amounts of virus inoculum. The level at which mutant coat protein resistance breaks down in comparison to the resistance conferred by the wild type coat protein can then be determined.

The amount of coat protein produced by each transgenic line can also be determined. Previous work has correlated levels of TMV coat protein expression with the degree of conferred resistance (7). For these experiments, the amount of transgene coat protein expression in relation to total plant protein can be determined. Total leaf protein from leaves of similar age and developmental stage can be extracted from each plant (33). Equivalent amounts of total leaf protein from each sample, determined by, for example, Bradford assay or other quantitative protein assay, can be subjected to polyacrylamide gel electrophoresis (PAGE) and Western blotting using established techniques. Polyclonal antiserum specific to virus coat protein can be used to detect the coat protein present in each sample. A scanning densitometer (such as Bio Rad Model GS670) can then be used to obtain a reading for coat protein bands present on the Western blot. This reading can be compared to readings from a set of known, virion purified, coat protein standards subjected to the same Western blot procedure. This information will yield the amount of coat protein per amount of total plant protein. This ratio will be determined for each plant tested, making it possible to compare levels of resistance to levels of expressed coat protein.

In summary, levels of resistance can be determined as the number of days required for the appearance of visual mosaic symptoms, confirmed by local lesion assay and ELISA. This can be compared to the relative amount of transgene coat protein accumulation in each line tested. Experiments can also be repeated using sequentially higher levels of inoculum for those lines showing resistance at the initial inoculum level. These experiments should clearly define any increase in resistance conferred by the transgene expression of disassembly deficient coat proteins.

The following example demonstrates a specific application of the general procedures described above. Such specific application can be used to modify the general procedures to allow protection against various virus types.

EXAMPLES

Production of Mutant Coat Proteins of TMV which Inhibit Disassembly of Wild Type Viruses Site-directed mutagenesis (22, 31, 32) and in vitro transcriptions (25, 26) were performed as previously described to generate the two mutant coat proteins of TMV. These mutants, designated TMV-D77N and TMV-E50Q contain an Asp77→Asn and a Glu50→Gln amino acid substitution, respectively. Transcription products were mechanically inoculated directly onto the leaves of *Nicatiana tabacum* L cv. Xanthi. Ten days after infection, virions were purified as described (27), with a final centrifugation step in a 10–40% sucrose density gradient. Coat proteins were isolated by acetic acid degradation (28). TMV-E50Q and TMV-D77N were both able to infect tobacco (cv. Xanthi). Their capacity to move systemically within the plants was markedly reduced. In fact, the time from inoculation to the appearance of symptoms on upper noninoculated leaves was more than two weeks, compared with only 5–7 days for wild type TMV. Systemic symptoms for E50Q and D77N also differed from the characteristic light-green dark-green mosaic produced by the wild type virus, appearing instead as sporadic yellow patches.

Virions extracted from leaf tissue infected by either coat protein mutant appeared by electron microscopy to be morphologically normal. Gel electrophoresis of RNA extracted from virions before density gradient purification showed, however, that the mutant virions contained very little RNA, compared with wild-type TMV. Even after density gradient purification, spectroscopic analysis showed that preparations of the TMV-E50Q virus-like particles contained only about 25% of the normal RNA complement ($OD_{260}/OD_{280} \approx 0.9$, compared with values close to 1.2 for wild type TMV). Preparations of purified TMV-D77N particles contained about 70% of the normal RNA complement ($OD_{260}/OD_{280} \approx 1.1$).

An assay for viral disassembly was developed, based on the exposure of RNA to ribonuclease. Earlier workers (21) had obtained excellent qualitative results by measuring progressive changes in sedimentation behavior, electron microscopic appearance and electrophoretic mobility and were able to show that the process of disassembly of TMV includes a number of stable intermediate particles. These assays were not quantitative, however, because any quantitative assay based on particle size would require a potentially unstable mathematical model that took into account the lengths and populations of all possible intermediate particles. Such an assay would also be affected adversely by errors in the measurement of the contributions of extensively or completely degraded particles. Results from sedimentation and electron microscopic assays would be further obscured by the presence of helical protein aggregates that did not contain RNA as noted above and such aggregates are significant contaminants of these mutant virion preparations. In order to avoid these problems, a simple, quantitative assay was developed in which the mount of viral nucleic acid freed from the disassembling virus particles was measured directly.

For disassembly assays, samples were dialyzed against at least 200 volumes of water overnight at about 5° and concentrations were determined by absorption at 260 nm, corrected for light scattering, using an extinction coefficient of 3.01 $mg^{-1}cm^2$ (35). The samples were adjusted to a concentration of 2.0 mg/ml, carbonate-bicarbonate buffer (pH 10.5) was added to 0.02M and the solution was kept an ice, with the removal of aliquots at intervals as required. Aliquots at zero incubation time were taken before addition of carbonate-bicarbonate buffer.

The aliquots were adjusted to pH 7.0±0.5 with 0.2M HCl and made 0.1M in KCl. Bovine pancreatic ribonuclease was added to about 3 µg/ml and digestion was allowed to proceed at room temperature for one hour. The pH was then reduced to 3.4±0.4, sufficient to observe turbidity due to aggregated protein and partially degraded virus. The samples were centrifuged for three hours at 400,000 g to remove protein and undegraded virus, then brought to pH 7.0±0.5 with 0.2M sodium carbonate. Absorption at 260 nm was used to determine free nucleotide concentrations, assuming an extinction coefficient for the mixture of nucleotides of $1.0 \times 10^4 M^{-1}cm^{-1}$.

Alkaline disassembly of TMV-D77N and wild type TMV was followed over a period of eight hours. TMV-D77N was significantly more stable than wild type TMV, exposing only about one-third the number of nucleotides at any given time. Alkaline disassembly of TMV-E50Q was not measured because of the small amounts of RNA in the particles.

Alkaline disassembly of wild-type TMV in the presence of excess wild type or mutant coat protein was also measured. These experiments were carried out as described above, except that all solutions were 0.1M in KCl, since overnight dialysis of TMV coat protein against water tended to cause denaturation of the protein. Disassembly of TMV under these conditions was not significantly affected by the presence of excess wild type coat protein, but it appeared to be reduced by TMV-D77N protein and was virtually abolished by TMV-E50Q protein.

Infectivity assays were performed by grinding 0.1 g of infected Xanthi tissue in 300 µl of 0.01M phosphate buffer, pH 6.8, at 0° C. A Carborundum-dusted half-leaf of the local lesion host *N. tabacum* cv. Xanthi-nc was inoculated mechanically with 50 µl of the plant extract. The other half-leaf was inoculated with wild-type TMV-infected plant extract as a control. Infectivity of purified virions was determined by inoculating each half-leaf with 50 µl of a solution containing 0.02 mg/ml virions. Infectivity was measured as the number of lesions produced on the half-leaf.

Infectivity from equivalent amounts of infected plant sap was markedly lower for TMV-E50Q and TMV-D77N than for wild type TMV (Table 1). The infectivity of purified TMV-D77N virions was also found to be significantly less than that of wild type virions. In contrast to wild type TMV, however, purified TMV-D77N virions maintained their levels of infectivity when the pH of the inoculum was raised from 7.0 to 9.0 (Table 1). Virion infectivity experiments were not performed for TMV-E50Q because of the small amounts of RNA in the particles.

In view of the ability of the mutant coat proteins to suppress wild-type TMV disassembly, their effect on the infectivity of wild-type TMV was also measured. Incubation of TMV virions at pH 8.0 is conducive to ribosome binding and it has been suggested that the process involves the removal of a small number of coat protein subunits from the 5' end of the RNA (36). Exposure of wild-type virions to pH 8.0 in the presence of excess mutant coat protein allows for the exchange of wild type for mutant protein subunits. Wild type virions (0.4 µg) were incubated with 4.0 µg of purified coat protein for 15 min in 0.01M Tris-HCl, pH 8.0. The pH was then adjusted with an equal volume of 0.1M Tris-HCl, pH 7.4 and the sample was incubated for an additional 30 min. Infectivity was determined as above, with half of each leaf receiving virions treated with excess wild-type coat protein, while the other half received virions treated with either excess TMV-D77N or TMV-E50Q coat protein. Incubation with excess TMV-D77N coat protein did not have any significant effect on the infectivity of wild-type virions, but the infectivity of wild-type virions incubated with excess TMV-E50Q coat protein was reduced by about 95% (Table 1).

Transgenic plants (*Nicotiana tabacura* cv. Xanthi) have been produced according to the methods described herein, which express TMV mutant coat proteins. These mutant coat proteins can protect these plants against TMV challenge to a greater degree than the protection demonstrated in transgenic plants expressing wild type coat proteins.

Throughout this application, various publications are referenced. The disclosures of these publications in their entireties are hereby incorporated by reference into this application in order to more fully describe the state of the art to which this invention pertains.

Although the present invention has been described with reference to specific details of certain embodiments thereof, it is not intended that such details should be regarded as limitations upon the scope of the invention except as and to the extent that they are included in the accompanying claims.

TABLE 1

| | | Infectivity Assays | | |
|---|---|---|---|---|
| Inoculum | Number of Leaves | Mean Lesions/ Half-Leaf | Control | Mean Lesions/ Half-Leaf |
| TMV-E50Q (plant extract) | 3 | 15.0 ± 2.2 (9.2) | TMV (plant extract) | >300 |
| TMV-D77N (plant extract) | 3 | 6.7 ± 1.5 (5.4) | TMV (plant extract) | >300 |
| TMV-D77N (purified virions) | 8 | 140.8 ± 4.2 (57.1) | TMV (purified virions) | 388.9 ± 6.8 (158.8) |
| TMV (pH 9) | 5 | 168.4 ± 5.8 (157.0) | TMV (pH 7) | 360.2 ± 8.4 (108.5) |
| TMV-D77N (pH 9) | 6 | 149.0 ± 6.0 (105.0) | TMV-D77N (pH 7) | 117.3 ± 4.4 (69.6) |
| TMV with E50Q protein | 8 | 5.3 ± 0.8 (3.2) | TMV with wild type protein | 111.8 ± 3.7 (81.3) |
| TMV with D77N protein | 8 | 32.9 ± 2.0 (10.3) | TMV with wild type protein | 34.3 ± 2.1 (12.9) |

Note: One-half of each leaf was inoculated with mutant TMV-infected plant extract or purified virions and the other half with an equivalent amount of the specified control. Numbers of local lesions given as >300 could not be accurately counted because lesions were confluent throughout the half-leaf. Mean numbers of lesions are given ± a standard deviation calculated as the square root of N/n, where n is the number of leaves observed, and N is the total number of lesions on all n half-leaves. This standard deviation calculation is based on the assumption that the number of lesions conforms to a Poisson distribution and that the relevant observation is the total number of lesions counted. The much larger standard deviation given in parenthesis is the more conventional standard deviation, calculated from the variation among half-leaves. This standard deviation is not, however, appropriate for a half-leaf assay. It measures primarily scatter among leaves, which is irrelevant to a half-leaf assay.

REFERENCES

1. Fraser, R. S. S. (1990) Ann. Rev. Phytopathol. 28:79
2. Powell-Abel, P. A. et al. (1986) Science 232:738
3. Beachy, R. N. et al. (1990) Ann. Rev. Phytopathol. 28:451–474
4. Fitchen, J. H. and Beachy, R. N. (1993) Ann. Rev. Microbiol. 47:739–763
5. Doughtery, W. G. et al. (1994)
6. Nelson, R. S. et al. (1987) Virology 158:126
7. Powell, P. A. et al. (1990) Virology 175:124
8. Stubbs, G et al. (1992) Abstract from FASEB meeting, Jul. 26–31, 1992, Vermont
9. Schardl, C. L. et al. (1987) Gene 61:1–11.
10. McCabe, D. E. et at. (1988) Bio Technology 6:923–926
11. Gregory, J. and Holmes, K. C. (1965) J. Mol. Biol. 13:796–801.
12. Namba, K. and Stubbs, G. (1985) Acta Cryst. A41:252–262.
13. Namba K. et al. (1989) J. Mol. Biol. 208:307–325
14. McPherson, A. (1982) *Preparation and Analysis of Protein Crystals* Wiley, New York.
15. Abad-Zapatero, C. et al. (1981) Acta Cryst. B37:2002–2018.
16. Silva, A. M. and Rossman, M. G. (1985) Acta Cryst. B41:147–157.
17. Stubbs, G. (1989) *Prediction of Protein Structure and Principles of Protein Conformation* Plenum, New York.
18. Caspar, D. L. D. (1963) Adv. Protein Chem. 18:37–121
19. Bancroft, J. B. (1970) Advan. Virus Res. 16:99–134
20. Wilson, T. M. A. (1984) Virology 137:255–265
21. Perham, R. N. et al. (1978) Virology 84:293–302
22. Geisselsoder, J. et al. (1987) Bio Techniques 6:786–791
23. Vieira, J. and Messing, J. (1987) Methods Enzymol. 153:3–11.
24. Goelet, P. et al. (1982) Proc. Nat. Acad. Sci., U.S.A. 79:5818–5822.
25. Ahlquist, P. and Janda, M. (1984) Mol. Cell. Biol. 4:2876–2882.
26. Dawson W. O. et al. (1986) Proc. Natl. Acad. Sci. U.S.A. 83:1832–1836.
27. Gooding, G. V., and Hebert, T. T. (1967) Phytopathology 57:1285.
28. Fraenkel-Conrat, H. (1957) Virology 4:1–4.
29. Maiti, I.B. et al. (1993) Proc. Natl. Acad. Sci. U.S.A. 79:5818–5822
30. Potrykus, I. (1991) Annual Rev. Plant Physiol. and Plant Molec. Biol. 42:205–225.
31. Culver, J. N. and Dawson, W. O. (1989) Mol. Plant-Microbe Interact. 2:209–213
32. Culver, J. N. et al. (1994) J. Mol. Biol. 242:130–138
33. Culver, J. N. and Dawson, W. O. (1991) Mol. Plant-Microbe Interact. 4:458–463
34. Perham, K. N. et al. (1976) FEBS Lett. 62:11–16
35. King, L. and Perham, R. N. (1971) Biochemistry 10:981–987
36. Wilson, T. M. A. (1984) Virology 137:255–265

What is claimed is:

1. A method of protecting plants against infection by pathogenic plant viruses comprising introducing into cells of the plant a nucleic acid, encoding a pathogenic plant virus protein, containing substitutions in the genetic sequence which result in the replacement of amino acids having carboxylate side chains which are in proximity with other amino acids having carboxylate side chains, such that they create electrostatic repulsive forces, with uncharged amino acids and which has the phenotypic effect of displacing wild type coat proteins in an infecting wild type virus in the process of disassembly and inhibiting the ability of the wild type virus to disassemble under conditions whereby the nucleic acid is expressed as a mutant coat protein within the plant.

2. A nucleic acid, encoding a pathogenic plant virus protein, containing substitutions in the genetic sequence which result in the replacement of amino acids having carboxylate side chains which are in proximity with other amino acids having carboxylate side chains, such that they create electrostatic repulsive forces, with uncharged amino acids and which, when expressed in a plant, has the phenotypic effect of displacing wild type coat proteins in an infecting wild type virus in the process of disassembly and inhibiting the ability of the wild type virus to disassemble, wherein the nucleic acid does not encode for asparagine at amino acid position 77 when the nucleic acid encodes a tobacco mosaic virus coat protein.

3. The nucleic acid of claim 2, wherein the nucleic acid is incorporated into a gene transfer vector.

4. The nucleic acid of claim 2, wherein the gene transfer vector is the binary Agrobacterium vector pKyLx71.

5. A plant functionally expressing the protein encoded by the nucleic acid of claim 2 in mounts which inhibit the ability of the wild type virus to disassemble.

* * * * *